(12) United States Patent
Lindsay

(10) Patent No.: US 8,029,728 B2
(45) Date of Patent: Oct. 4, 2011

(54) BLOOD PERFUSION AIR REMOVAL DEVICE WITH ARCUATE MANIFOLD

(75) Inventor: Erin Jessica Lindsay, Ann Arbor, MI (US)

(73) Assignee: Terumo Cardiovascular Systems Corp., Ann Arbor, MI (US)

( * ) Notice: Subject to any disclaimer, the term of this patent is extended or adjusted under 35 U.S.C. 154(b) by 1576 days.

(21) Appl. No.: 11/245,752

(22) Filed: Oct. 7, 2005

(65) Prior Publication Data

US 2006/0029514 A1 Feb. 9, 2006

Related U.S. Application Data

(63) Continuation-in-part of application No. 11/118,726, filed on Apr. 29, 2005, now Pat. No. 7,588,723.

(60) Provisional application No. 60/692,148, filed on Jun. 20, 2005, provisional application No. 60/573,923, filed on May 24, 2004.

(51) Int. Cl.
*A61M 1/00* (2006.01)
*A61M 37/00* (2006.01)

(52) U.S. Cl. .......................... 422/44; 604/4.01; 604/6.15

(58) Field of Classification Search .............. 422/44–48; 604/4.01–6.16, 8–10; 137/15.26; 210/247, 210/304

See application file for complete search history.

(56) References Cited

U.S. PATENT DOCUMENTS

| 1,734,507 | A | | 10/1928 | Westling et al. |
| 3,599,659 | A | * | 8/1971 | Nuter et al. ................... 137/202 |
| 4,299,248 | A | | 11/1981 | Becker et al. |
| 4,555,253 | A | | 11/1985 | Hull et al. |
| 5,379,795 | A | | 1/1995 | Hartley et al. |
| 5,386,844 | A | | 2/1995 | Kennedy |
| 5,429,595 | A | * | 7/1995 | Wright et al. ...................... 604/9 |
| 5,484,474 | A | * | 1/1996 | Weinstein et al. .............. 96/209 |
| 5,824,212 | A | | 10/1998 | Brockhoff |
| 6,019,824 | A | | 2/2000 | Schnell |
| 6,248,231 | B1 | | 6/2001 | Di Bella et al. |
| 6,517,732 | B1 | | 2/2003 | Brockoff et al. |
| 6,562,107 | B2 | | 5/2003 | Purdom et al. |

* cited by examiner

*Primary Examiner* — Tatyana Zalukaeva
*Assistant Examiner* — Philip Wiest
(74) *Attorney, Agent, or Firm* — Gael Diane Tisack, Esq.; Mark L. Mollon, Esq.; Darryl Newell

(57) ABSTRACT

An air removal device removes air from blood flowing in a perfusion system. A generally cylindrical chamber has a liquid flow region at a lower end thereof and has a gas collection region at an upper end thereof. An arcuate manifold provides an arcuate flow path outside of the chamber having an upstream end and a downstream end. A slit aperture is provided between the arcuate manifold and the chamber along at least a substantial portion of the arcuate manifold. A mixture of gas and liquid introduced into the arcuate flow path at the upstream end flows through the slit aperture to create a spiral flow within the chamber causing the gas to move toward a central axis of the chamber and into the gas collection region.

4 Claims, 13 Drawing Sheets

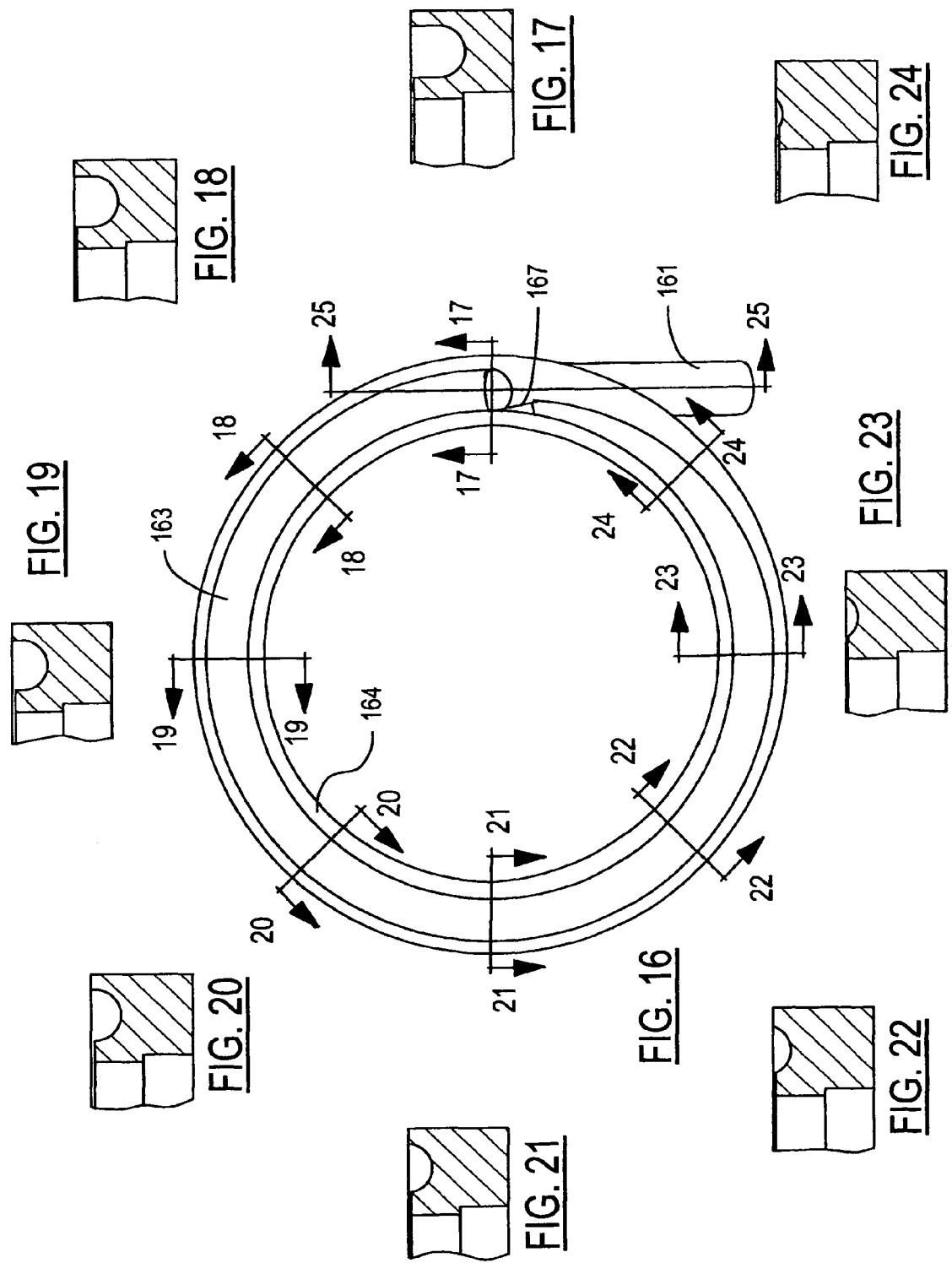

BLOOD PERFUSION AIR REMOVAL DEVICE WITH ARCUATE MANIFOLD

CROSS REFERENCE TO RELATED APPLICATIONS

This application claims priority to co-pending U.S. provisional application Ser. No. 60/692,148, filed Jun. 20, 2005, and is a continuation-in-part of U.S. nonprovisional application Ser. No. 11/118,726, filed Apr. 29, 2005 now U.S. Pat. No. 7,588,723, which claims priority to U.S. provisional application Ser. No. 60/573,923, filed May 24, 2004.

STATEMENT REGARDING FEDERALLY SPONSORED RESEARCH

Not Applicable.

BACKGROUND OF THE INVENTION

The present invention relates in general to extracorporeal blood perfusion systems, and, more specifically, to an air removal device for separating entrained air from blood flowing in the system under control of a float-driven lever arm.

When heart surgery is performed 'on pump', steps are taken to remove air entrained in the blood flowing in the extracorporeal blood circuit. Preferably, air removal occurs upstream of the pump. Typically, either a cardiotomy reservoir with defoamer or a flexible venous reservoir (FVR) has been employed. An FVR typically comprises a sealed bag with a luer valve or stopcock at its upper end for manually removing excess air. A cardiotomy reservoir comprises a hard shell for collecting and storing blood which is then supplied to the pumped system. The collection chamber is open to atmosphere and the blood is at atmospheric pressure. Any air bubbles in the blood rise to the top of the collection chamber. Blood is resident in the reservoir for a time that is sufficiently long for air to separate. A blood defoamer is often mounted in the reservoir to aid in the breakdown of foam bubbles in the chamber. Substantially bubble-free blood is drawn out of the reservoir at the bottom. The cardiotomy reservoir can also be used for filtration of particulates or for addition of fluids or pharmacological agents.

Blood from a patient can be collected passively or actively. Passive drainage is accomplished by catheterizing the patient, connecting the catheter with tubing to a cardiotomy or FVR, and siphoning the blood into the cardiotomy or FVR. Active drainage is accomplished by using either a pump or vacuum source on the drainage line to pump or suction blood from the access site. The resulting blood flow rate is greater than what is obtained using passive drainage. When drainage is passive, the pressure in the extracorporeal circuit upstream of the blood pump typically becomes slightly positive relative to atmospheric. When drainage is active, the pressure in the circuit upstream of the pump frequently becomes less then atmospheric. Either a cardiotomy or FVR may be used when drainage is passive. An FVR will not work during active drainage because the negative pressure in the circuit will cause the FVR to collapse.

Certain advantages could be realized by eliminating the use of the cardiotomy reservoir. For instance, a reduction in blood contacting surface areas, a reduction of blood to air interface, a reduction of fluid priming volume of the perfusion circuit, and elimination or reduction of the amount of blood-to-defoamer contact are all expected to improve patient outcome. Since an FVR provides a closed system (i.e., not open to atmosphere) it can achieve some of these advantages to a certain degree, but it cannot be used when active drainage is desired because of the tendency to collapse under negative pressure.

Closed, hard shell reservoirs have recently been suggested for use as air removal devices. These systems have required an active electronic sensor such as an ultrasonic sensor for detecting the presence of collected air and an electronically controlled purge valve that is triggered when air is sensed. However, cost and potential reliability issues associated with active sensing and purging are disadvantageous. No system has yet met the objectives of removing air from blood flowing at high flow rates in a passive manner (i.e., without electronic sensors) and doing so whether the pressure within the system is higher or lower than atmospheric pressure.

SUMMARY OF THE INVENTION

The present invention provides an air removal device and method with low prime volume, efficient air removal, and minimal exposure of blood to a defoamer. The device described herein does not collapse under negative pressure and can be used in place of a venous reservoir for both passive and active drainage procedures.

In one aspect of the invention, an air removal device is provided for removing gas from a liquid, such as air from blood flowing in a perfusion system. A generally cylindrical chamber has a liquid flow region at a lower end thereof and has a gas collection region at an upper end thereof. An arcuate manifold provides an arcuate flow path outside of the chamber having an upstream end and a downstream end. A slit aperture is provided between the arcuate manifold and the chamber along at least a substantial portion of the arcuate manifold. A mixture of gas and liquid introduced into the arcuate flow path at the upstream end flows through the slit aperture to create a spiral flow within the chamber causing the gas to move toward a central axis of the chamber and into the gas collection region.

BRIEF DESCRIPTION OF THE DRAWINGS

FIG. 16 is a top view of the inlet manifold.

FIGS. 17-25 are cross-sectional views of the inlet manifold taken at the cross sections indicated in FIG. 16.

DETAILED DESCRIPTION OF PREFERRED EMBODIMENTS

Figure 1:
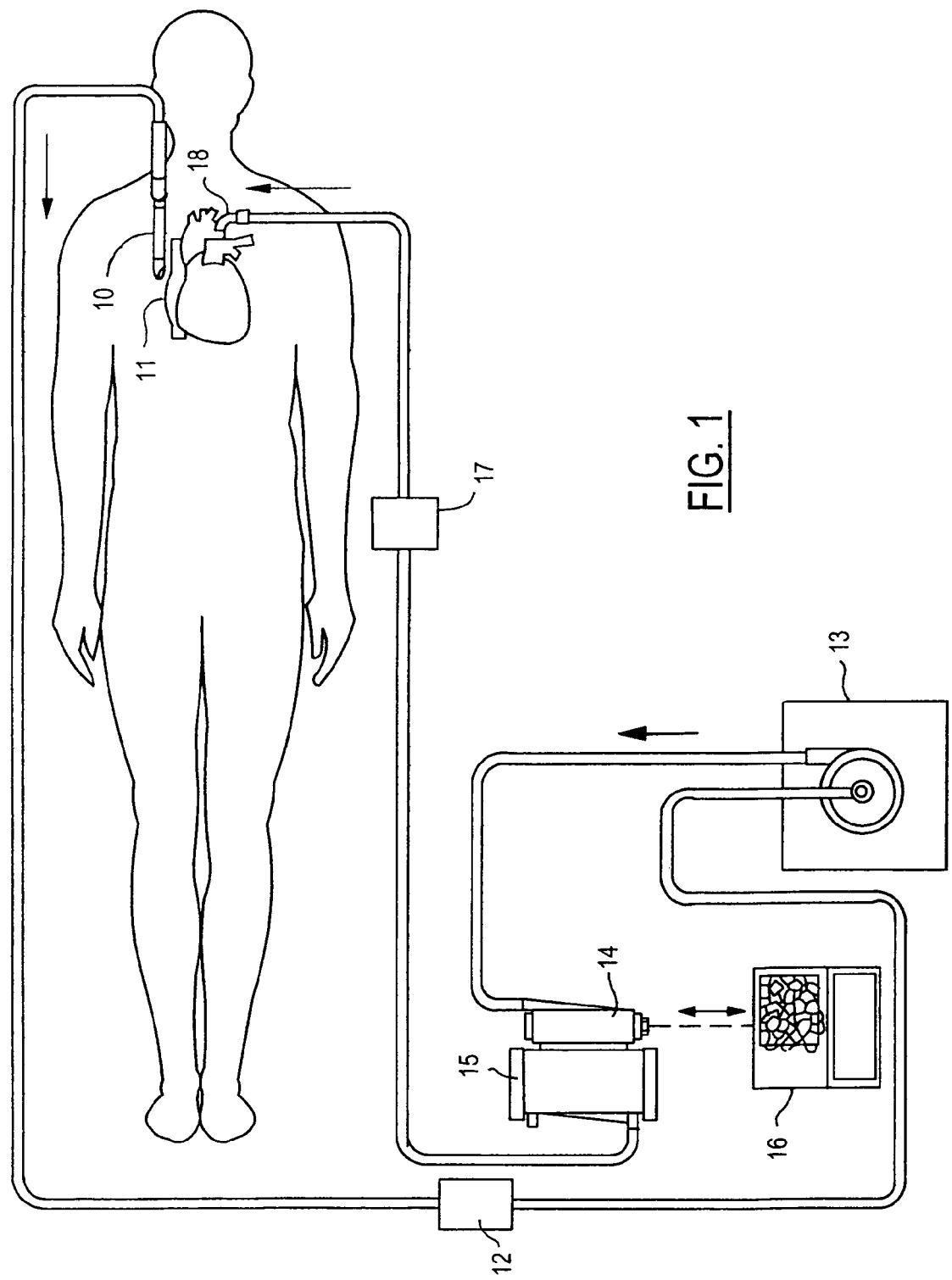
FIG. 1 is a diagrammatic view of a perfusion system of the present invention.

FIG. 1 shows a simplified diagram of a perfusion system for supporting on-pump coronary artery bypass graft surgery. A venous catheter 10 is inserted at 11 into the superior or inferior vena cava. Venous blood flow is driven by an arterial pump 13 which may be comprised of a centrifugal pump, for example. Blood passes through a heat exchanger 14 and then to an oxygenator 15. A blood heater/cooler 16 is connected to heat exchanger 14 for selectably heating or cooling blood as is required during different phases of surgery. Oxygenated blood is conducted to an arterial cannula 18 to return the oxygenated blood to the patient's aorta.

Air in the form of a bolus or bubbles can be introduced into the blood at the point of extraction from the body due to a leak around the venous catheter, for example. It is desirable to remove entrained air prior to the blood entering the oxygenator. Thus, an air removal device 12 is preferably inserted into the venous line. Rather than or in addition to air removal device 12, an air removal device 17 may be used in the arterial side of the circuit.

Figure 2:
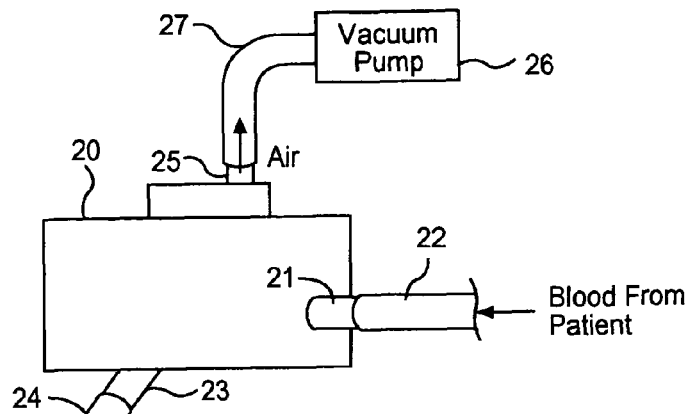
FIG. 2 is a diagrammatic view of an air removal device of the present invention.

Among other objectives, the present invention seeks to minimize prime volume of the perfusion circuit as well as reducing surface area of blood contact and the exposure of blood to air (the air/blood interface). It is further desirable to handle large volumes of both air and blood while removing large amounts of air in a short period of time while using a device that does not collapse when the circuit pressure is below atmospheric pressure. FIG. 2 shows an air separator device 20 having an inlet 21 connected to a flow line 22 for receiving a blood/air mixture from the patient and a blood outlet 23 connected via a flow line 24 to an arterial pump. An air outlet 25 is connected to a vacuum pump 26 via an air removal line 27. Device 20 preferably uses a rigid body for withstanding negative pressure present in an active system.

Figure 3:
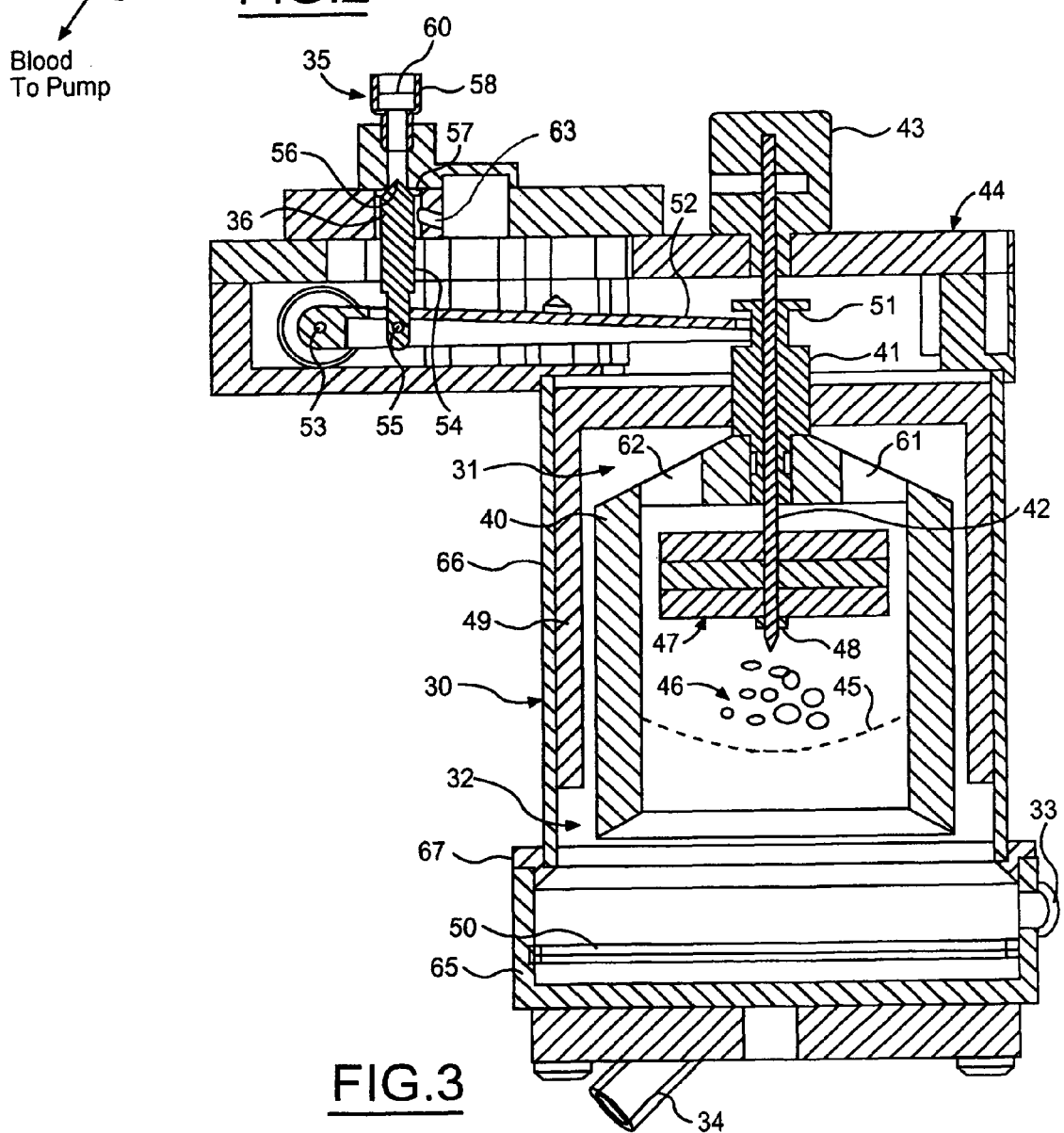
FIG. 3 is a cross-sectional view of a first embodiment of an air removal device.

FIG. 3 is a schematic, cross-sectional view illustrating the main functional elements of the present invention. A main chamber 30 comprises a rigid housing with a cylindrical interior space that has an upper air collection region 31 and a lower blood flow region 32. An inlet 33 and an outlet 34 preferably provide a tangential flow into and out of chamber 30 in order to create a spiral flow path. Preferably, inlet 33 is vertically higher than outlet 34. An air outlet 35 from chamber 30 is vertically higher than inlet 33. A valve 36 opens and closes air outlet 35 as described below.

A float 40 is attached to a bushing 41 that is slidably mounted to a guide rod 42 in air collection region 31. Guide rod 42 is suspended from a mounting block 43 attached to a lever housing 44.

In order to float on blood passing through the device, float 40 has an effective density (i.e., weight divided by total displacement volume) less than the density of blood. When blood (or priming fluid) is being pumped through the perfusion circuit, fluid enters chamber 30 up to a variable fluid level 45. The centrifugal blood flow within chamber 30 created by the tangential input causes air bubbles 46 to migrate toward the central vertical axis of chamber 30. Air buoyancy causes it to further migrate upward to the air collection region. When the volume of air (e.g., from separated bubbles) within chamber 30 increases, the level of blood in the device decreases and float 40 moves down from its vertically highest position. To assist in breaking up bubbles or foam in air collection region 31, a blood defoamer stack 47 is retained on guide rod 42 by a nut 48 and a blood defoamer cup 49 is affixed to the interior wall of chamber 30. Conventional defoamer material may be utilized, e.g., a sponge of about 10 ppi density coated with silicone surfactant. Defoamers 47 and 49 are sufficiently spaced from float 40 and bushing 41 (e.g., by gaps of about 0.05 inches) that their up and down movement is not affected by any friction or changes in buoyancy.

To assist in removing air from the blood, a mesh screen 50 is disposed across chamber 30 between inlet 33 and outlet 34. The mesh of screen 50 allows blood to flow from inlet 33 to outlet 34 but blocks air bubbles having a size greater than the mesh spacing. The mesh size of screen 50 may be in the range of about 32 mesh to about 80 mesh, for example.

Bushing 41 has a groove 51 for receiving one end of a lever arm 52. The other end of lever arm 52 is connected to a pivot pin 53 within housing 44. Lever arm 52 rotates about pivot pin 53 by following the float-driven up and down motion of groove 51. At an intermediate portion of lever arm 52 between its two ends, a valve stem 54 is rotatably mounted by a pivot pin 55. At the opposite end of stem 54, a needle (e.g., conically-shaped) end surface engages an o-ring seal 57 thereby creating a needle valve which is closed when float 40 is at its highest vertical position and is open when float 40 is below that position. Preferably, air outlet 35 includes a vacuum fitting 58 for connection to a vacuum source (not shown). An optional hydrophobic membrane 60 may be provided across the interior passage way of fitting 58 in order to prevent any liquids from reaching the vacuum source. An overflow chamber (not shown) may also be provided between valve 36 and air outlet 35 to divert liquids from the vacuum source.

In order to ensure easy air flow between air collection region 31 and air outlet 35, air escape holes 61 and 62 are provided in the top surface of float 40. Furthermore, an air feed passage 63 is provided from the interior of housing 44 and the upper end of valve 36 so that air can flow relatively unimpeded to air outlet 35 when valve 36 is open.

Chamber 30 includes a bottom cup-shaped section 65 and an upper cylinder section 66 connected by an intermediate ring 67. In one preferred embodiment, bottom section 65 may have an inside diameter of about 4 inches and a depth of between about 0.5 and 1 inch. Cylinder 66 is only slightly smaller in internal diameter than bottom section 65. Cylindrical section 66 accommodates float 40 having an outer diameter of about 2.9 inches, and inside diameter of 2.1 inches, and a height of about 3.5 inches. Float 40 is preferably press fit or glued onto bushing 41 which has a central bore diameter of about 0.1 inches. Guide rod 42 may be comprised of brass and have a diameter of about 0.093 inches. Thus, bushing 41 freely rides up and down on guide rod 42 so that the forked end of lever arm 52 which is captured in groove 51 follows the up and down movement.

Lever arm 52 is preferably comprised of a light weight plastic. Stem 54 pivotally connected to lever arm 52 may be comprised of brass and engages a central bore of the valve seat that has a diameter of about 0.1 inches.

During use, if there is no excess air being extracted from blood passing through the device, the float remains in its upward position with the vacuum source closed off. Blood swirls between the inlet and outlet and migrates through the holes in the mesh screen and into the outlet port on its way to the blood pump. However, when air bubbles enter the chamber, the less dense air is forced to the center of the chamber and upward by the centrifuge affect of the swirling blood. The air bubbles rise up the hollow center of the float and contact defoamer stack 47 or rise up outside of float 40 and contact defoamer cylinder 49. As the volume of air in the chamber increases, the level of blood drops enough so that the float and bushing drop below their maximum height and the needle valve opens to remove excess air.

Vacuum applied to the air outlet valve tends to resist the downward motion of the float. However, the mechanical amplification of the weight of the float by the lever arm greatly reduces the ability of the suction forces to prevent downward movement of the float. Downward movement of the forked end of the lever arm pulls the needle away from the seal seat, allowing negative pressure from the vacuum source to enter the chamber. The negative pressure pulls air bubbles upward and the escaping air is evacuated. Once enough air has been pulled from the device to allow the float to rise, the vacuum is closed off again.

Figure 4:
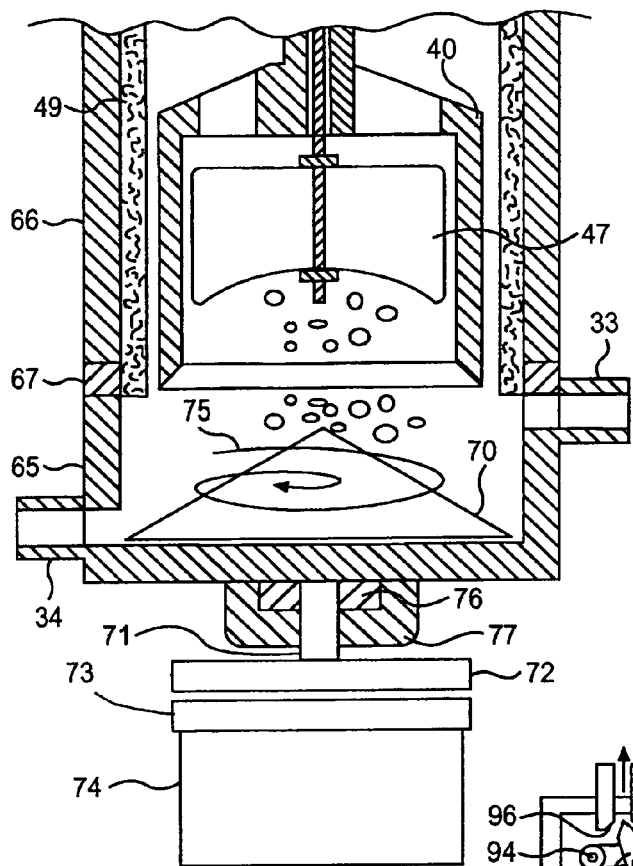
FIG. 4 is a cross-sectional view of a second embodiment of an air removal device.

FIG. 4 shows an alternative embodiment for increasing the centrifugal effect to more efficiently remove air bubbles from blood. A cone 70 is rotatably mounted at the bottom section 65. A shaft 71 couples cone 70 to a first half of a magnetic coupler 72. The other half of coupler 73 is connected to a motor drive 74 which is user controlled in order to rotate in the same direction as the tangential blood flow from inlet 33. As cone 70 spins, the centrifugal flow is enhanced as shown by arrow 75. Bearings 76 and seal 77 are provided for reducing friction during rotation and for preventing leakage.

Other features such as spirally-shaped guide channels within the blood flow chamber can also be used to enhance centrifugal separation of blood and air.

Figure 5:
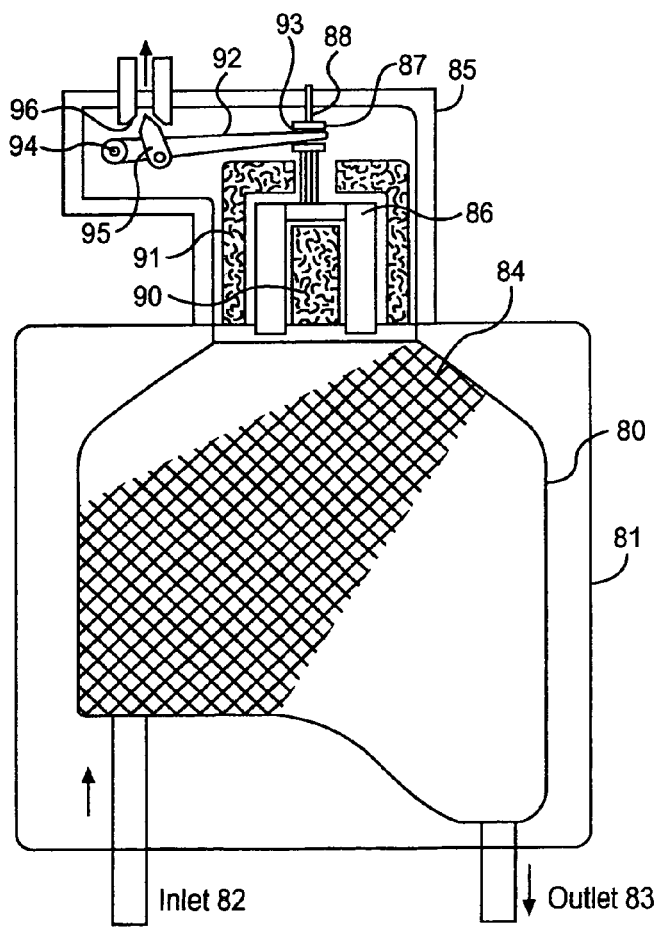
FIG. 5 is a cross-sectional view of a third embodiment of an air removal device.

The lever arm and valve of the present invention can be utilized for extracting air that has been separated from the blood by any mechanism, not just by centrifugal flow. Thus, an alternative embodiment in FIG. 5 utilizes a flexible venous bag 80 mounted within a rigid plastic case 81. Blood from an inlet 82 flows into bag 80 and out through an outlet 83. A mesh screen 84 is disposed in bag 80 between inlet 82 and outlet 83 with its edges sealed to the sides of bag 80 so that all flow paths at the lower end of bag 80 from inlet 82 to outlet 83 pass through screen 84. The upper momentum of blood entering inlet 82 encourages bubbles to flow to the top of bag 80. Blood drawn downward out of outlet 83 must pass through screen 84, thereby further removing entrained air bubbles. The bubbles flow to the top of bag 80 where the float valve and lever arm of the present invention are disposed. Thus, a housing 85 contains a float 86 coupled to a hub 87 slideably mounted on a guide rod 88. Defoamers 90 and 91 are provided inside and outside of float 86, respectively. A lever arm 92 extends between a groove 93 in hub 87 and a pivot point 94. A needle valve including a stem 95 pivotally joined to lever arm 92 and a valve seat 96 operate as in the previously described embodiments.

Figure 6:
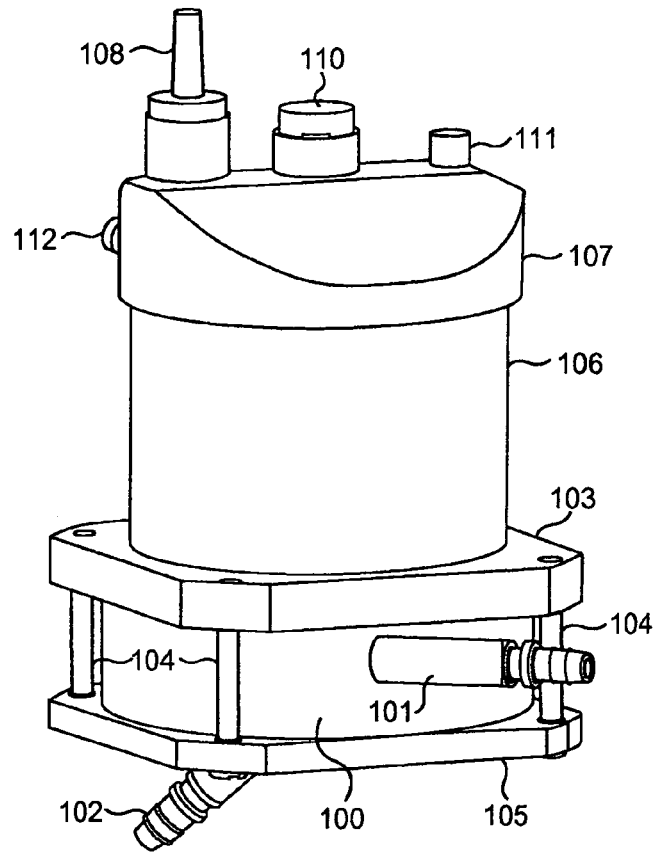
FIG. 6 is a front perspective view of another embodiment of an air removal device.
Figure 7:
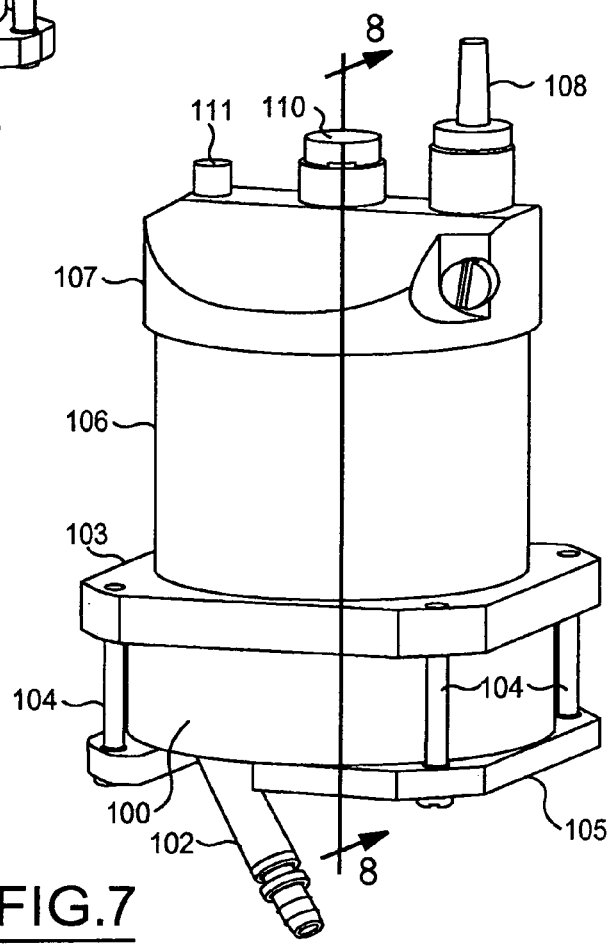
FIG. 7 is a rear perspective view of the device of FIG. 6.

Yet another embodiment is shown in front and rear perspective views in FIGS. 6 and 7. A blood flow housing 100 has an inlet 101 oriented tangentially and an outlet oriented tangentially and canted downward. A top cover 103 is disposed on top of housing 100 and is clamped thereto by screws 104 passing through a bottom plate 105. A cylinder 106 is disposed within a central aperture of cover 103 for housing a float. A lever arm cover 107 is affixed to cylinder 106 and has an air outlet 108. Lever housing 107 also receives a guide rod 110 and has an auxiliary port 111. A pivot screw 112 passes through an internal cavity of lever arm cover 107 to provide the pivot point of the lever arm as described below. During normal usage, auxiliary port 111 is closed off by a plug. Port 111 allows direct access to the interior chamber (e.g., for pressure testing, priming, introduction of treatment fluids, or other purposes).

Figure 8:
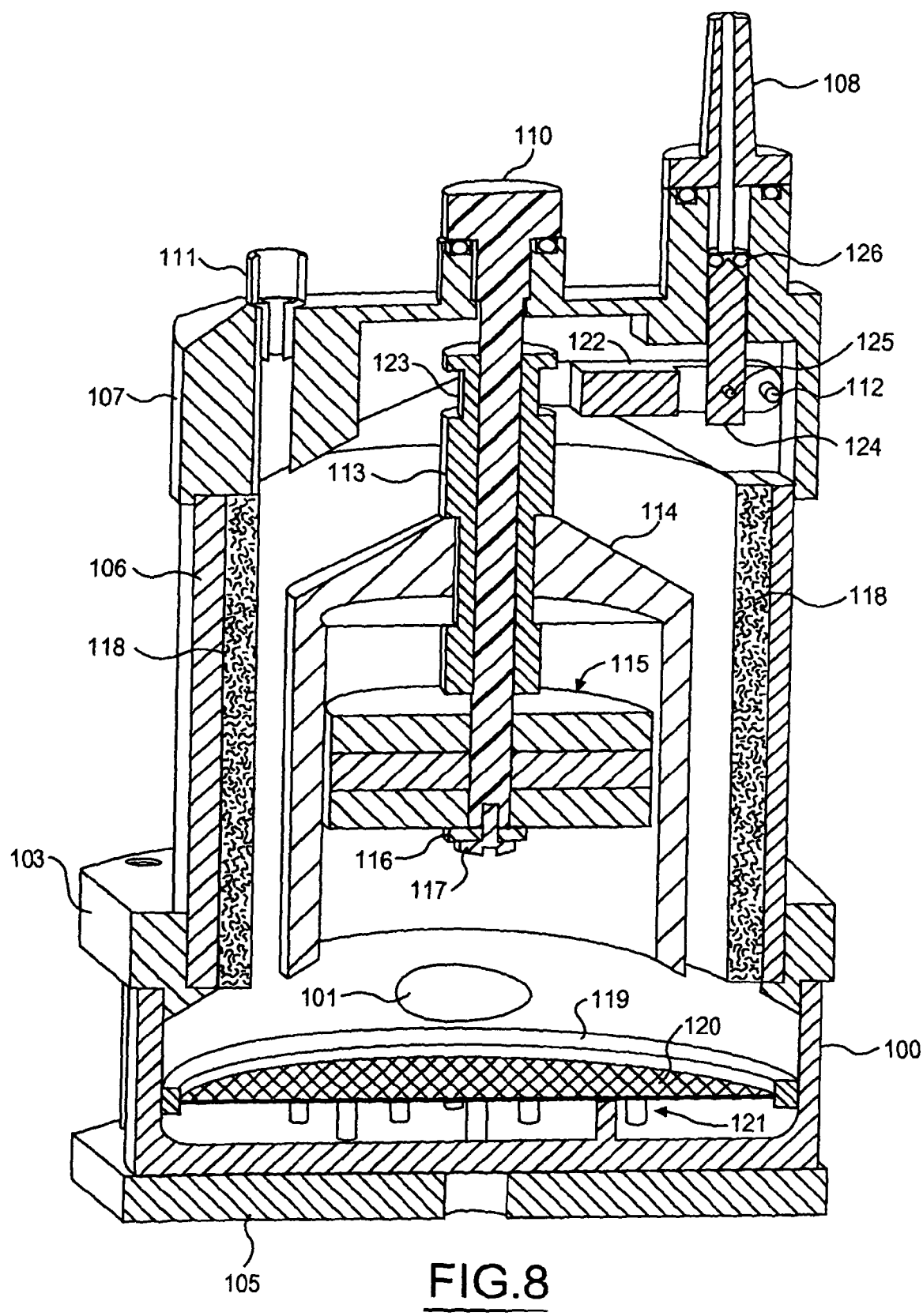
FIG. 8 is a cross-sectional view seen along line 8-8 of FIG. 7.

The device of FIGS. 6 and 7 is shown in cross section in FIG. 8. Guide rod 110 slidably receives a hub 113 that carries a float 114. At the lower end of guide rod 110, a stack 115 of defoamer disks is retained by a washer 116 and screw 117. A defoamer cylinder 118 is mounted to the inner side of cylinder 106.

A screen within flow housing 100 includes a circular frame 119 for retaining a mesh 120. Frame 119 is preferably joined to the inner wall of housing 100 using an adhesive, for example. Support posts 121 are integral with housing 100 for supporting mesh 120 against the blood flow.

A lever arm 122 extends between pivot screw 112 and a groove 123 in hub 113. Valve stem 124 is joined to lever arm 122 by a pin 125. An o-ring seal 126 receives a needle-shaped end of stem 124 for closing off air outlet port 108.

Figure 9:
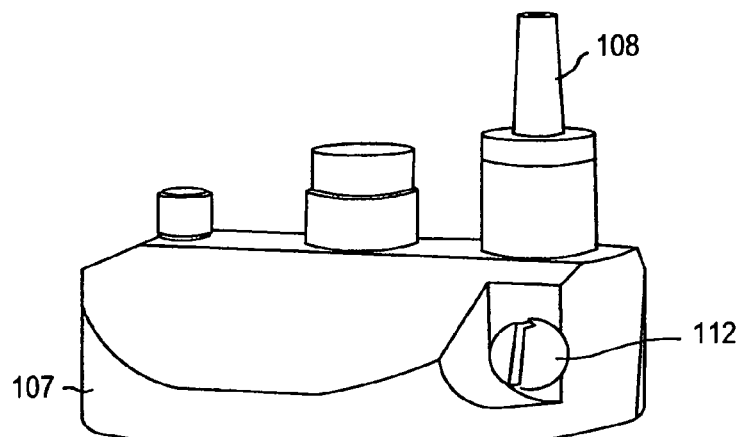
FIG. 9 is a rear perspective view of the lever arm subassembly.
Figure 10:
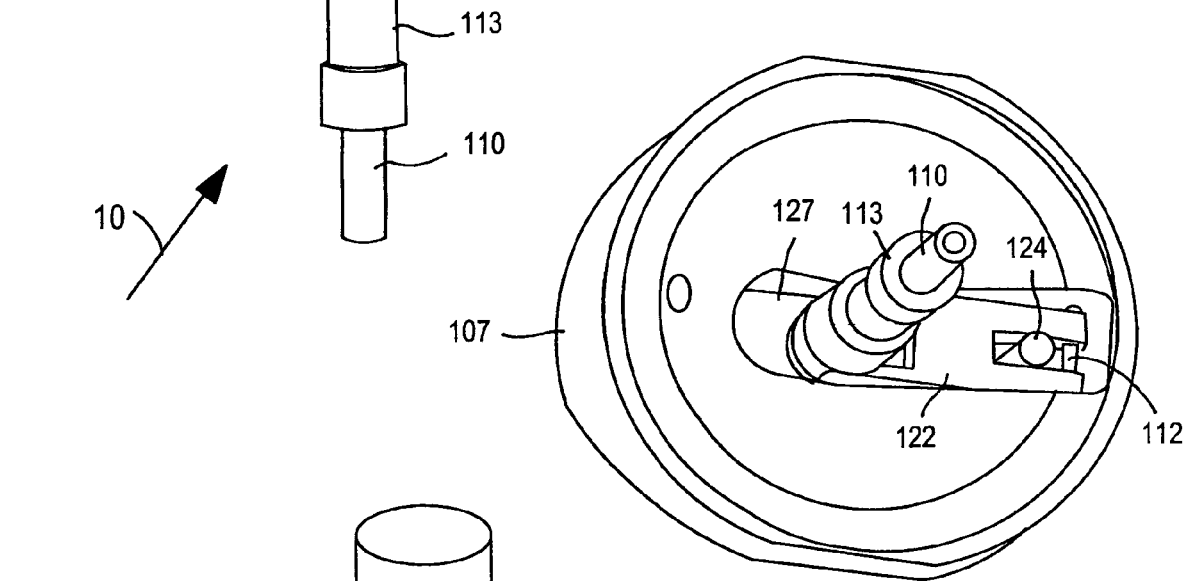
FIG. 10 is a bottom perspective view seen along arrow 10 in FIG. 9.
Figure 11:
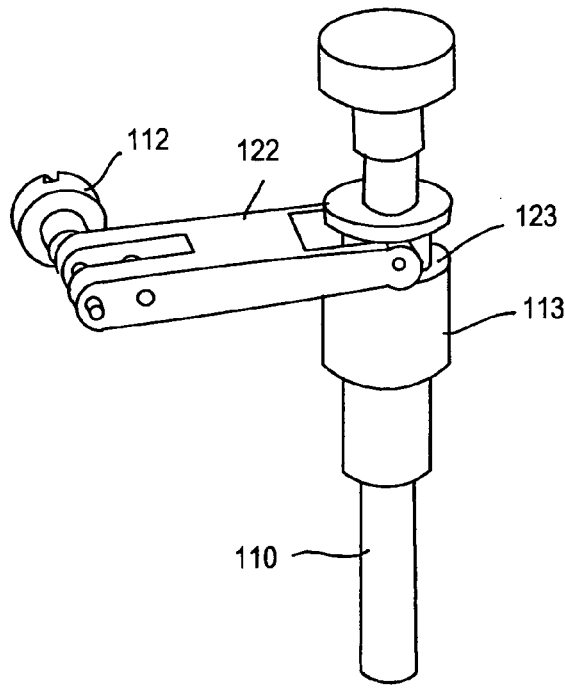
FIG. 11 shows components causing the lever arm to pivot.

FIG. 9 shows guide rod 110 mounted to lever arm cover 107 with hub 113 being mounted on guide rod 110. As shown in the bottom view of FIG. 10, a recess 127 in cover 107 has a slotted shape for accommodating lever arm 122. FIG. 11 shows how pivot screw passes through a pair of aligned holes in one end of lever arm 122 to establish the pivoting of lever arm 122 to follow the float-driven movement of groove 123 in hub 113.

Another preferred embodiment is shown in FIGS. 12-25 for providing high efficiency air removal in a compact device. In particular, an improved inlet to the main separation chamber provides an increased cross-sectional area resulting in a lower blood flow velocity and reduced mixing.

Figure 12:
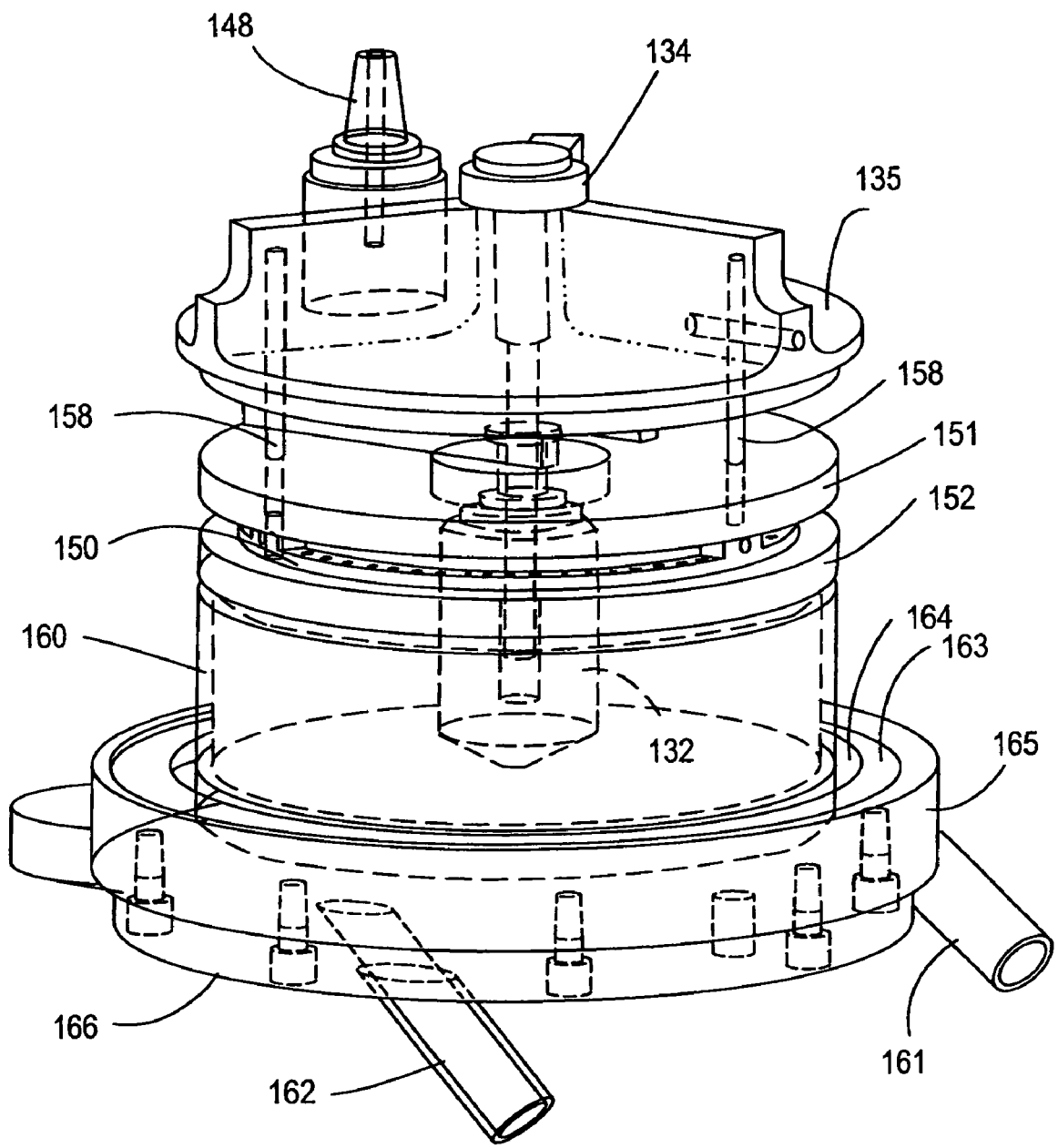
FIG. 12 is a front perspective view of another preferred embodiment of an air removal device with its outer cylinder wall removed and having an inlet manifold.
Figure 13:
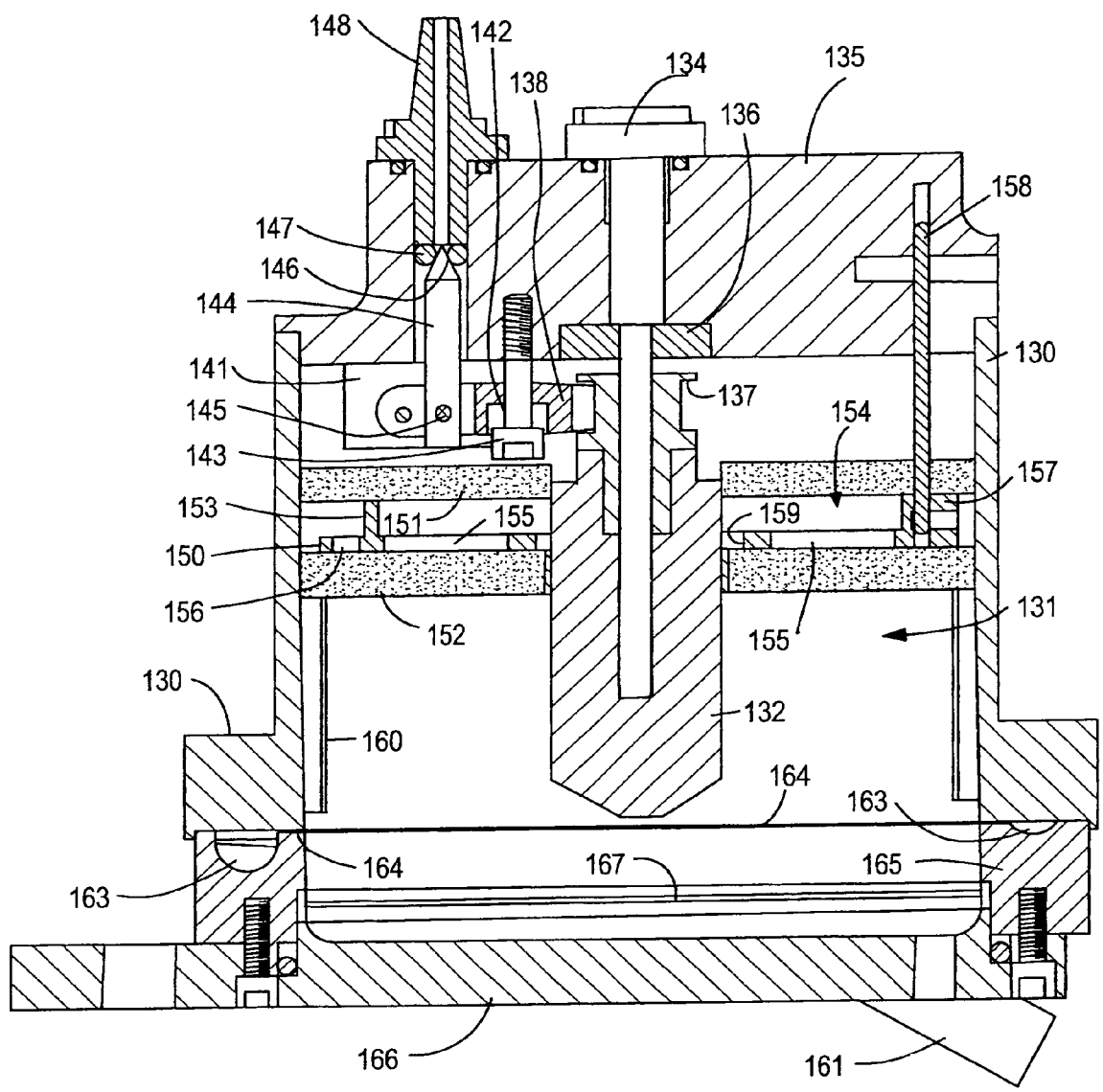
FIG. 13 is a central cross-sectional view of the device of FIG. 12.
Figure 14:
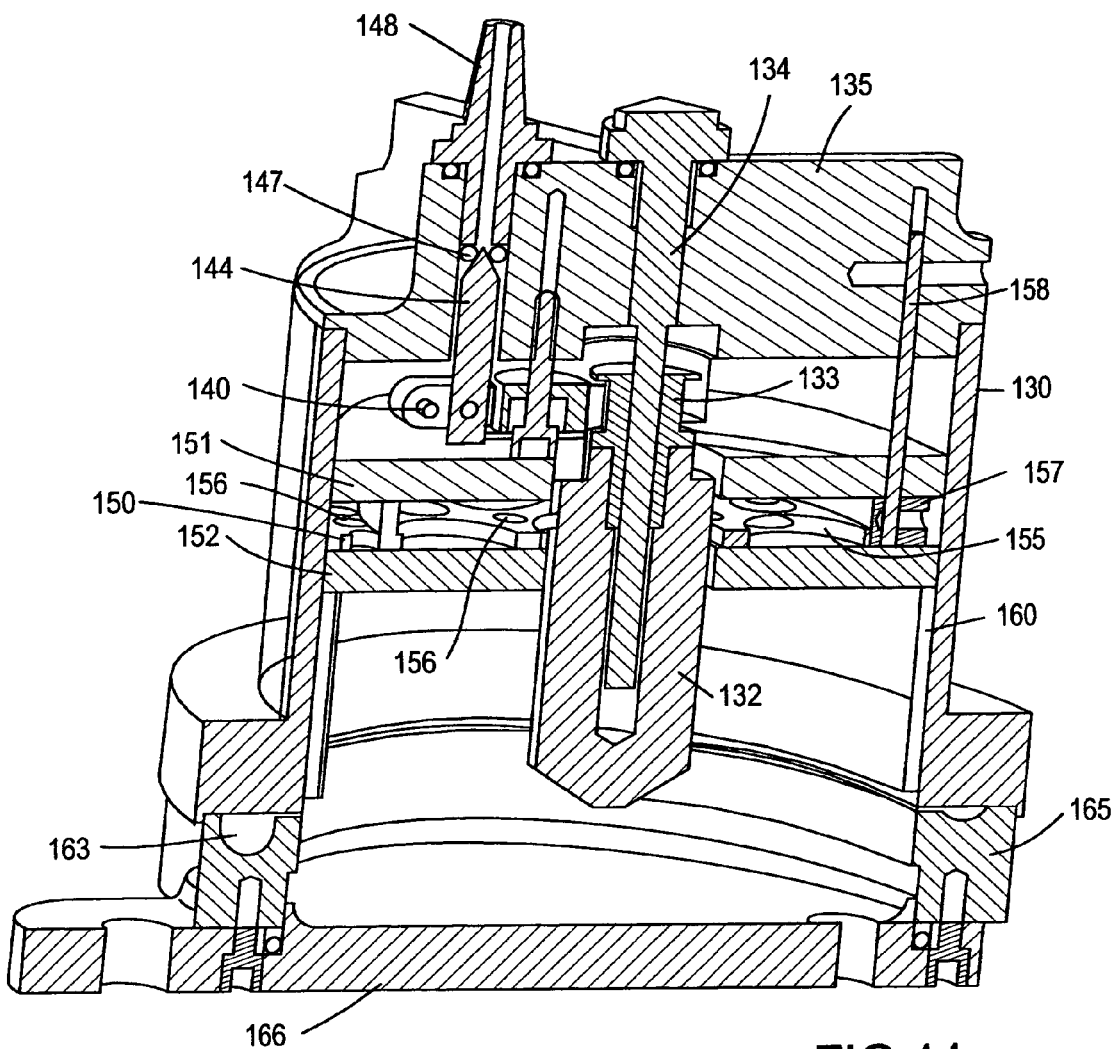
FIG. 14 is a perspective central cross-sectional view of the device of FIG. 12.

Referring to FIGS. 12-14, an outer cylindrical wall 130 (removed in FIG. 12 to show interior components) encloses a cylindrical chamber 131 where a spiral blood flow achieves air removal through centrifugal density separation. A solid-center, buoyant float 132 may preferably be about 12 grams in weight. A bushing 133 is attached to float 132 and has a central bore aligned with a central bore of float 132. The bores slidingly receive a guide rod 134 mounted through a cover member 135 and secured by a retainer 136. Bushing 133 includes an annular groove 137 for receiving a forked end of a lever arm 138. The other end of lever arm 138 rotates about a pivot pin 140 extending from a baffle 141 on the bottom side of cover member 135. Lever arm 138 may preferably be about 1.40" in length from pivot centerline to guide rod centerline so that it fits easily within a cylindrical wall have an inside diameter of about 4".

Lever arm 138 includes a limit stop 142 comprising a horizontal plate with a hole for receiving a set screw 143 screwed into cover member 135. When the head of set screw 143 contacts limit stop 142, further downward motion of lever arm 138 and float 132 is prevented.

Lever arm 138 is connected to a valve stem 144 by a pin 145. Valve stem 144 includes a needle (e.g., conically-shaped) end surface 146 for engaging an o-ring seal 147 thereby creating a needle valve which is closed when float 132 is at its highest vertical position and is open when float 132 is below that position. An air outlet port 148 may be connected to a vacuum source (not shown).

A defoamer support grid 150 is attached to two layers of reticulated polyurethane sponge 151 and 152 each coated with silicone surfactant conventionally used in blood reservoir defoamers. Each layer may be about ¼ inch thick and have a porosity of about 5 PPI (pores per inch). Layer 152 resides adjacent the bottom surface of grid 150 and layer 151 resides adjacent the upper surface of grid 150. Grid 150 may be about 0.100 inch thick and has a ring 153 extending near its outer perimeter to approximately 0.200 inch above upper surface.

Ring 153 prevents upper sponge layer 151 from touching the upper surface of grid 150, thus creating an air space 154 in which bubbles can combine, break their individual surface tension, and release air while allowing the blood film to drain back down through bottom layer 152 to combine with the liquid blood in the lower regions of the device. A plurality of perforations are located in grid 150 including large perforations 155 permitting upward air travel and downward blood draining and small perforations 156 (e.g., about 0.190 inch in diameter located around the outside perimeter of grid 150 and around the perimeter of central hole 159) for sewing or otherwise attaching layers 151 and 152 to grid 150. Alternative to being sewn, layers 152 and 152 can be secured to grid 150 by clips, barbs, glue, or other means. Grid 150 further includes mounting supports 157 for receiving a plurality of vertical attachment posts 158 extending from cover member 135 to maintain grid 150 in a fixed location. Grid 150 could alternatively be held in its vertical location by attaching it directly to the cylinder inner walls or by other means.

The "sandwich" formed by grid 150 and layers 151 and 152 is sized so as to contact the entire perimeter wall of cylinder 130. This prevents bubbles from escaping up and around the outer perimeter of the sponges. Furthermore, a cylindrical sponge 160, also comprised of reticulated polyurethane coated with silicone surfactant, is mounted against cylinder wall 130 abutting layer 152. Sponge 160 may be retained by gluing, a retention ledge (not shown) molded into cylinder wall 130, or other suitable means.

During operation, blood enters the cylinder at a lower inlet port and rises in the cylinder to a level just below the bottom surface of the lower sponge. The blood level will remain relatively constant with the volume of the entering blood being substantially equal to the volume of blood exiting the cylinder through an outlet port in the floor of the cylinder. Even though blood is entering and exiting the cylinder, the float will remain in its upper position, the needle valve will be closed and the vacuum (negative pressure) will be prevented from entering the cylinder. In the event that air bubbles entrained in the blood come into the cylinder by means of the inlet port, the float will drop to a point that lever arm 138 is pulled downward thereby pulling needle valve 146 from contact with o-ring seat 147. This action creates a negative pressure inside the cylinder and pulls the blood upward which also causes the air inside the bubbles to expand, thereby helping to break their surface tension and causing them to rupture. The combination of contact with the surfactant and the sudden exposure to negative pressure provides an efficient mechanism for bubble bursting.

With the inherent mechanical advantage of a lever arm, the size of the float can be reduced to a low weight (e.g., 12 grams) while still providing sufficient leverage to pull the needle from the o-ring seat even with a vacuum source of up to about 300 mm of Hg. The advantage of reducing the float size is that more defoaming sponge surface area can be provided in a cylinder of a given diameter (i.e., by minimizing the float volume, defoaming performance is maximized).

A mixture of blood and entrained air is supplied to the device via a tubular inlet fitting 161 and de-aerated blood is removed via a tubular outlet fitting 162. Each fitting may comprise a ⅜ inch diameter port oriented substantially tangentially with respect to the cylinder in order to establish a vortex flow within the cylinder. The inlet further comprises an arcuate manifold 163 providing an arcuate blood flow path outside of chamber 131 and a slit aperture 164 between arcuate manifold 163 and chamber 131. Arcuate manifold 163 has an upstream end and a downstream end. Slit aperture 164 extends along at least a substantial portion of arcuate manifold 163, preferably over the full length of manifold 163. Preferably, manifold 163 and slit aperture 164 utilize substantially all of the circumference around chamber 131, thus creating a substantially 360° entry of blood/air mixture into the cylinder which reduces turbulence and does not promote mixing as is seen in single, high velocity inlet ports.

Arcuate manifold 163 may comprise a channel formed into a top surface of a manifold ring 165. The inside upper edge of the top surface of manifold ring 165 is at a lower height so that when ring 165 is mounted against cylindrical wall 130, the resulting gap forms slit aperture 164. Inlet port 161 does not directly communicate with chamber 131 but instead connects to arcuate manifold 163 to inject a tangential, annular flow into the manifold.

A bottom cover 166 is attached to manifold ring 165 and forms the bottom surface of chamber 131. Outlet fitting 162 projects from bottom cover 166 substantially tangentially and downward to extract blood flow with very little or no remaining air. A mesh screen 167 may be retained in a notch between ring 165 and bottom cover 167.

In a preferred embodiment, arcuate manifold 163 covers approximately 355° of the circumference just outside of chamber 131. Slit aperture 164 preferably comprises a gap of about 0.010 inch to about 0.060 inch and covers 360° of the circumference. As blood/air mixture enters the annular manifold, it travels in a circular manner through the manifold tunnel. Since there is a substantially continuous slit aperture through which blood/air mixture can escape sideways into the chamber, there is no concentrated jet stream into the chamber. Blood and bubbles enter the cylinder for essentially the entire 360° of the slit aperture. The cross-sectional area of the slit entry into the chamber is preferably larger than the cross-sectional area of a single inlet port. In the case of a ⅜ inch diameter inlet port conventionally used in blood circuits, the area is 0.110 square inches. In a preferred embodiment using a 0.040 inch wide gap and a 4 inch diameter cylinder, the slit cross-sectional area is 0.50 square inches. The larger cross section greatly reduces the velocity of the blood/air mixture as it enters the chamber.

As the incoming blood/air mix travels through the arcuate manifold, it escapes through the slit aperture and into the cylinder with a slightly helical vector which imparts a rotation to the blood residing in the cylinder. The rotation is in the range of approximately 50 to 400 rpm with blood flow rates of up to about 7 liters per minute. This rotation, coupled with a very low velocity, uniform inlet "sheet-flow" profile, combine to create a very good centrifugal action that works to gently push any air bubbles toward the center of the chamber. The relatively low velocity creates less tendency for incoming air bubbles to contact the mesh screen which defines the floor of the air removal portion of the cylinder.

Forcing the blood/air mixture through a slit aperture promotes coalescing of bubbles (i.e., combining bubbles by eliminating the film separating one bubble from an adjacent one). The combining of air bubbles promotes buoyancy such that the enlarged bubbles more quickly and efficiently rise to contact the surfactant coated sponge. This preliminary combining of many of the bubbles tends to cooperate beneficially with the gentle "whirlpool" centrifugal rotation of the blood within the cylinder to improve the efficiency of the air bubble removal.

Figure 15:
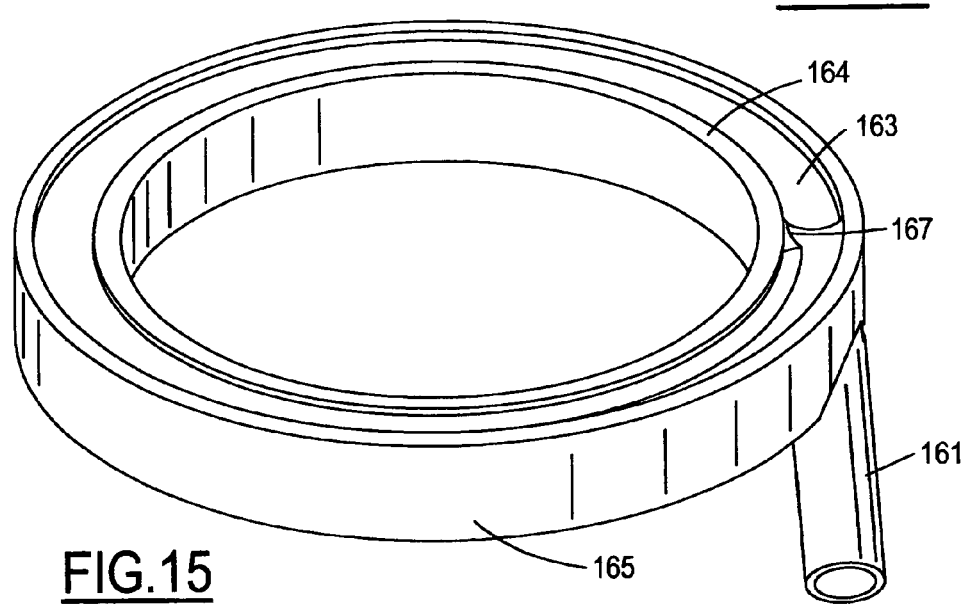
FIG. 15 is a perspective view of the inlet manifold.

Manifold ring 165 is shown in greater detail in FIGS. 15 and 16. The simplest cross-sectional profile of manifold tunnel 163 would be constant throughout its length. Likewise, slit aperture 164 can have a constant gap size and constant radial span. For example, the arcuate manifold tunnel may have a substantially round cross section of about 0.110 square inches while the slit aperture has a constant gap of about 0.040 inch and a radial land distance between the manifold tunnel and the chamber of about 0.150 inch.

As the incoming blood/air mix gradually escapes sideways through the slit aperture, there will be less and less need for a large cross section within the manifold because the flow demand will be progressively less. By the time the flow has reached a location about 355° past the upstream end, there will be very little flow required to travel inside the manifold. To optimize the flow profile and reduce prime volume to conserve blood, the manifold cross section may preferably be variable. As shown in FIGS. 15 and 16, manifold 163 preferably has a cross-sectional area that is generally decreasing from the upstream end to the downstream end. For example, it starts at about 0.110 square inch and gradually decreases to about 0.005 square inch at a location about 355° from the upstream end.

The slit aperture gap width and radial length can also vary to optimize flow distribution into the chamber.

Slit aperture 164 is placed intermediate between the defoaming sponge 151 and mesh screen 167. A low, medium or high aperture position within this range is possible, with a preferred location of about 25% the way up from the screen (e.g., approximately 0.350 inch from screen 167 and about 1.30 inch from sponge 151). Alternatively, the aperture could be placed nearer the top surface of the blood pool within chamber 131. This could help place air bubbles at the surface more efficiently with less chance of inadvertently contacting the screen before they have a chance to rise to the blood surface.

The channel of manifold 163 preferably has an end ramp 167 at the downstream end for terminating the channel and directing any remaining flow into chamber 131 by gradually decreasing the depth and radial length of the channel to zero. Thus, the upstream end and downstream end are substantially isolated by end ramp 167. End ramp 167 may extend from about 355° to about 360° from the upstream end, for example.

Figure 25:
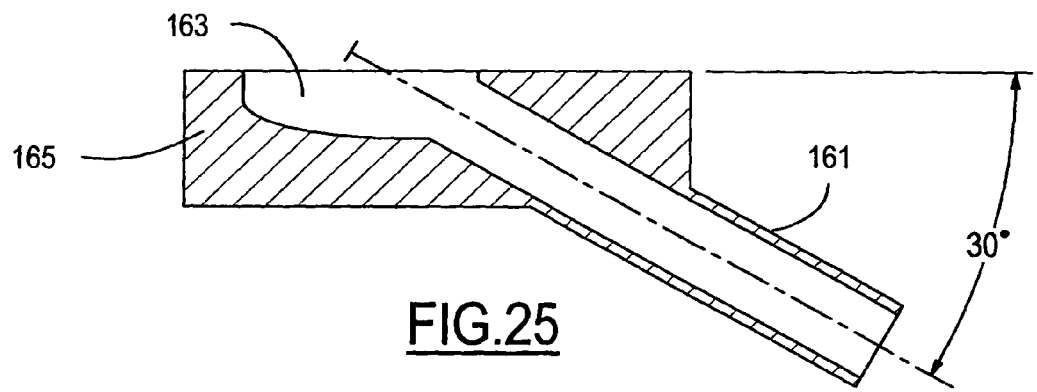

FIGS. 18 through 24 illustrate the gradually diminishing cross-sectional area of manifold 163. Both the depth and the radial width of the tunnel can be decreased to achieve the reduction in cross section, or either one alone can be decreased. FIG. 25 shows tubular inlet fitting 161 joining into arcuate manifold channel 163. The passage within fitting 161 is substantially tangential with respect to the cylinder and is preferably angles-upward into the channel at an angle of about 30° from horizontal, for example.

Figure 26:
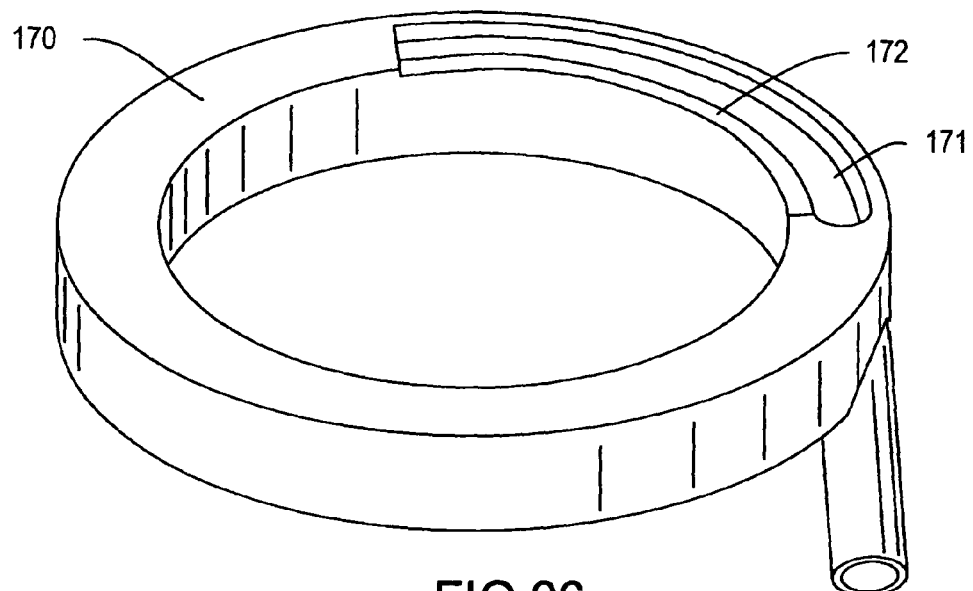
FIG. 26 is a perspective view of an alternative embodiment of the inlet manifold.

FIG. 26 shows an alternative embodiment wherein a manifold ring 170 includes an arcuate manifold channel 171 extending over about 90° of the circumference. An aperture slit 172 may provide a large gap as compared with the previous embodiment in order to maintain a desirably high slit cross section. The arcuate manifold can extend for any circumferential distance, but preferably greater than about 30° in order to avoid jet-like mixing at the entry to the chamber. Arcuate manifold 171 has a cross-sectional area that remains substantially constant from the upstream end to the downstream end, although a tapered cross section can alternatively be used.

Figure 27:
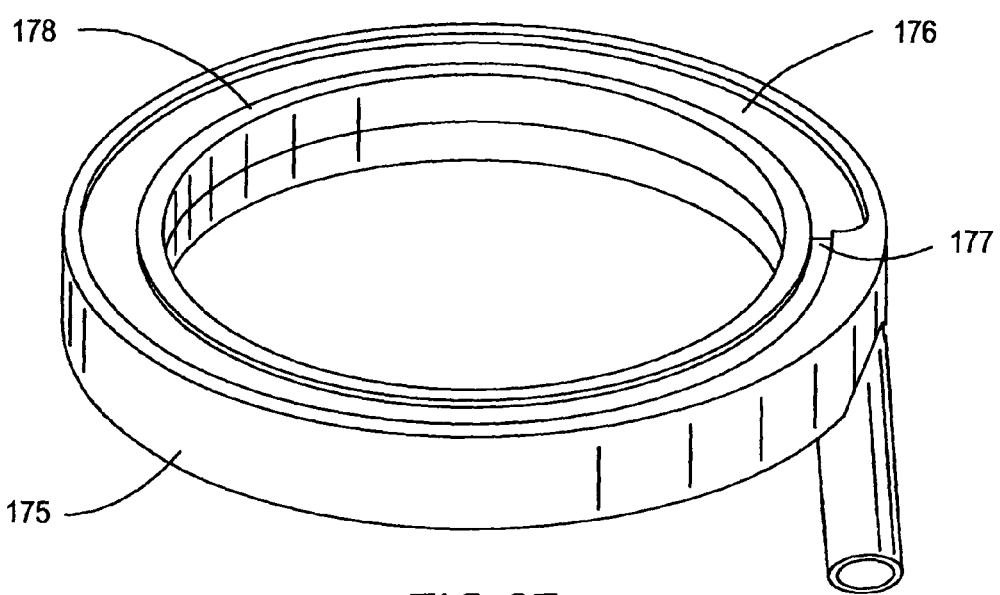
FIG. 27 is a perspective view of another alternative embodiment of the inlet manifold.
Figure 28:
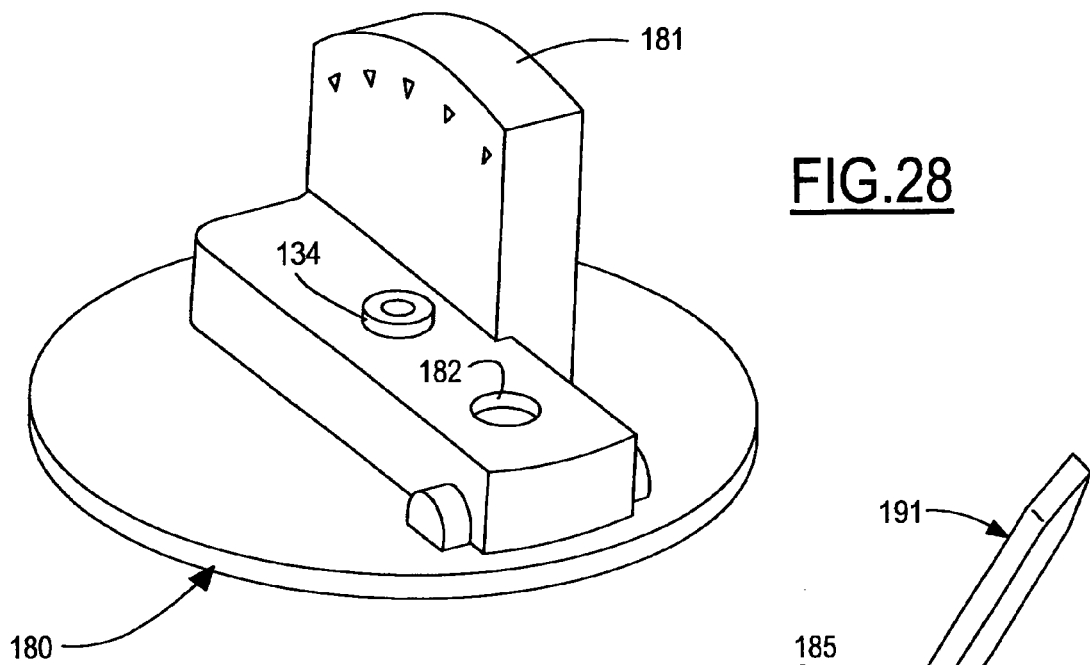
FIG. 28 is a top perspective view of a cover member in another alternative embodiment having blood level indication.

FIG. 27 shows another alternative embodiment wherein a manifold ring 175 includes an arcuate manifold channel 176 extending over the complete 360° of the circumference so that the downstream end feeds back into the upstream end. A full annular path is formed by providing an open passageway 177. Consequently, both manifold 176 and slit aperture 177 are continuous around manifold ring 175.

Even when the housing and cover member of the air removal device are formed from a clear plastic, it may be difficult to see the actual blood level in the device or to know when the float is correctly dropping to open the needle valve so that air is removed.

Therefore, a further embodiment is shown in FIGS. 28-32 wherein a level indication mechanism is provided. A cover member 180 shown in FIGS. 28 and 30 has a clear, hollow housing extension 181 along the side of a lever-arm recess 194. Guide rod 134 is mounted to cover member 180. An aperture 182 receives air outlet port 148.

Figure 29:
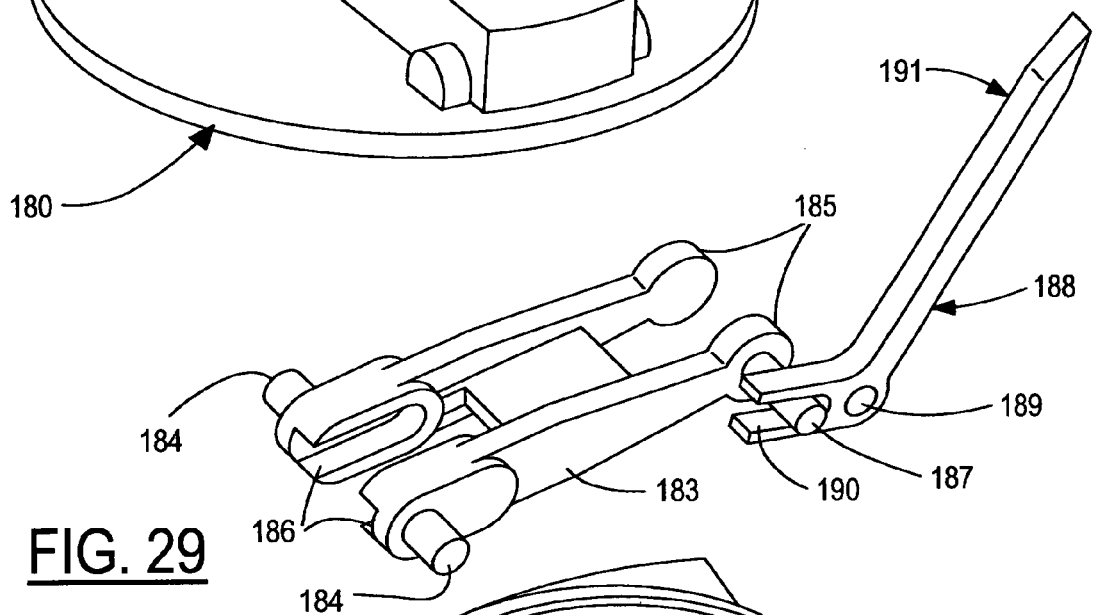
FIG. 29 is a perspective view of a lever arm and pointer.
Figure 30:
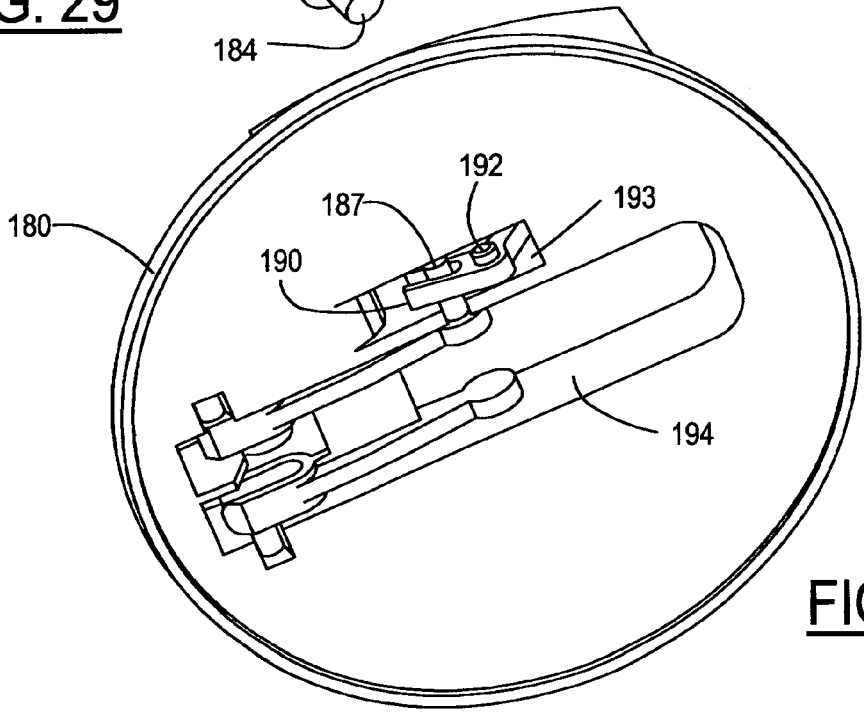
FIG. 30 is a bottom perspective view of the lever arm and pointer of FIG. 29 installed in the cover member of FIG. 28.
Figure 31:
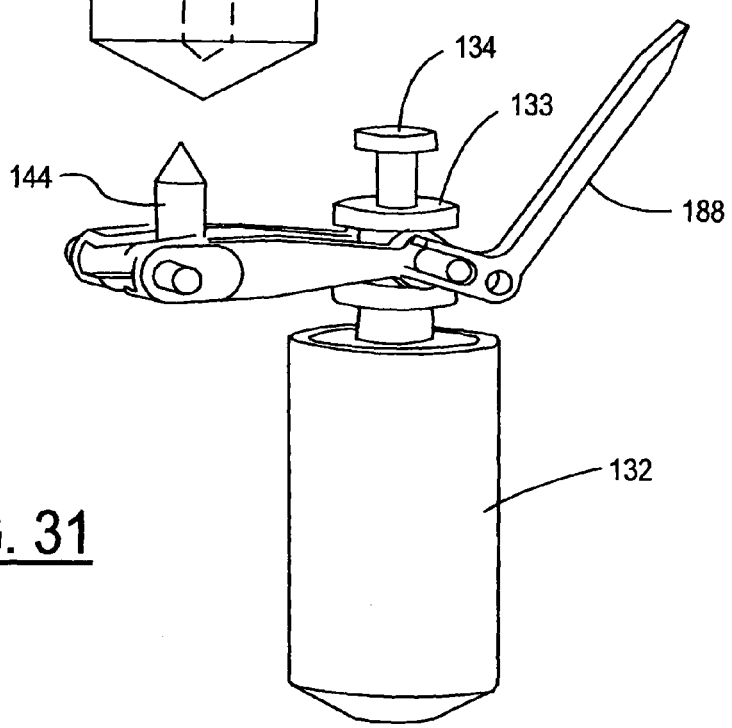
FIG. 31 shows the lever arm and pointer joined with the float.

A lever arm 183 is shown in FIG. 29 having pivot pins 184 at one end and projections 185 for fitting onto the float bushing at the other end (see FIG. 31). Grooves 186 receive transverse mounting pins of a valve stem so that the valve stem motion is offset from the pivot axis of pivot pins 184. A drive pin 187 extends from lever arm 183 at one forked end 185 and is captured in a drive slot 190 of a pointer 188. An aperture 189 is located intermediately between drive slot 190 and an indicator arm 191. As shown in FIG. 30, aperture 189 is mounted over a post 192 that extends from an inside wall 193 of housing extension 181. Indicator arm 191 moves along an arc within housing extension 181 in response to up and down movement of float 132.

Figure 32:
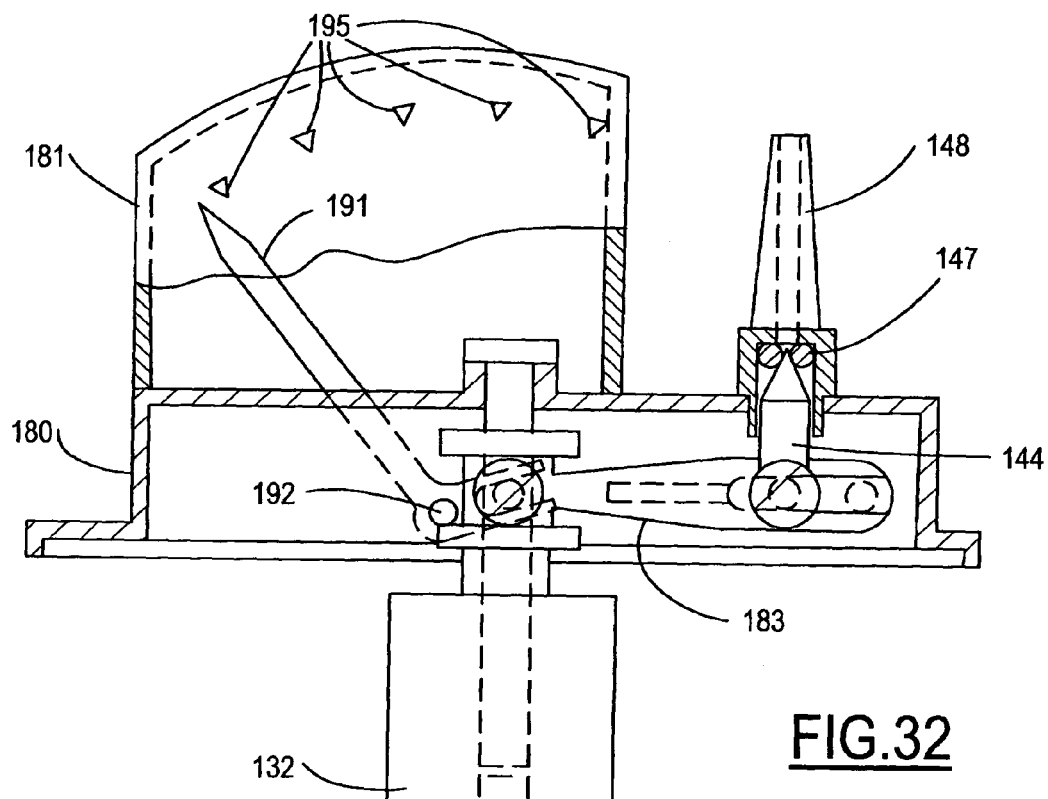
FIG. 32 is a partial, front cross-section of the embodiment having level indication.

As seen in cross section in FIG. 32, indicator arm 191 sweeps an arc behind a plurality of volume indicators 195 that may be embossed or painted to the clear plastic exterior of housing extension 181. A scale showing actual volume could also be included such that the full volume is labeled at the left and the partial volume corresponding to when the float just begins to float on the blood being labeled at the right side of the scale. The up and down movement of float 132 simultaneously controls the opening and closing of valve stem 144 against o-ring 147 and the pivoting of indicator arm 191 on post 192. By visually monitoring the position of indicator arm 191 in relation to indicators 195, a user can determine the actual functioning of the air removal device during use.

While the arcuate manifold of the present invention is particularly beneficial for separating air from blood in a perfusion system, it will be appreciated that it can also be used for separating other fluids of differing densities, such as other liquids and gasses.

What is claimed is:
1. An air removal device for removing air from blood flowing in a perfusion system, comprising:
   a cylindrical chamber having a blood flow region at a lower end thereof and having an air collection region at an upper end thereof, said chamber further having an inlet, a blood outlet, and an air outlet vertically higher than said inlet;
   a vertical guide structure in said air collection region;

a float disposed for vertical movement following said vertical guide structure, wherein said float has an effective density less than the density of said blood;

a lever arm having a first end for following vertical movement of said float and having a second end pivotally mounted at a pivot point stationary with respect to said vertical guide structure; and a valve coupled to said air outlet and to an intermediate point of said lever arm between said first and second ends for closing said air outlet when said float is at its vertically highest position wherein said inlet comprises an arcuate manifold providing an arcuate blood flow path outside of said chamber having an upstream end and a downstream end and a slit aperture between said arcuate manifold and said chamber, said slit aperture extending along at least a substantial portion of said arcuate manifold.

2. The device of claim 1 wherein said inlet further comprises:

a tubular fitting fluidically coupled to said upstream end of said arcuate manifold arranged substantially tangentially with respect to said arcuate manifold.

3. The device of claim 1 wherein said arcuate manifold comprises a channel having an end ramp at said downstream end for terminating said channel and wherein said annular path and said slit aperture extend for substantially 360° with said end ramp substantially isolating said downstream end from said upstream end.

4. The device of claim 1 wherein said arcuate manifold has a cross-sectional area that is generally decreasing from said upstream end to said downstream end.

* * * * *